United States Patent [19]

Swindells et al.

[11] 4,120,818
[45] Oct. 17, 1978

[54] IRREVERSIBLE WARMUP INDICATOR

[75] Inventors: Frank E. Swindells, Arlington, Va.; Mary G. Klimas, Fort Pierce, Fla.,

[73] Assignee: The United States of America as represented by the Secretary of the Army, Washington, D.C.

[21] Appl. No.: 713,312

[22] Filed: Aug. 10, 1976

[51] Int. Cl.² .................................. C09K 3/00
[52] U.S. Cl. ............................ 116/114 V; 116/114.5; 252/408
[58] Field of Search ............... 252/408; 116/114.5, 116/114 Y; 73/356, 358, 114 V; 23/253 TP

[56] References Cited

U.S. PATENT DOCUMENTS

| 1,535,536 | 4/1925 | McDonald | 116/114.5 |
| 2,560,537 | 7/1951 | Andersen | 116/114.5 |
| 3,981,683 | 9/1976 | Larsson et al. | 116/114 Y |
| 4,028,944 | 6/1977 | Erb | 73/358 X |

Primary Examiner—Benjamin R. Padgett
Assistant Examiner—J. L. Barr
Attorney, Agent, or Firm—William G. Gapcynski; Werten F. W. Bellamy; Sherman D. Winters

[57] ABSTRACT

A device for indicating irreversibly by means of color change that temperatures equal to or above 7° C, 10° C, or 13° C have occurred. A container which has an orifice therein is filled with a liquid which freezes at the temperature to be monitored. A dye is dissolved in the liquid. The orifice is placed in proximity to an indicating paper. When the container is activated by freezing, any increase in temperature after activation causes the liquid to melt, expand and escape through the orifice contacting the indicating paper thereby dying the paper and producing an irreversible signal.

10 Claims, 4 Drawing Figures

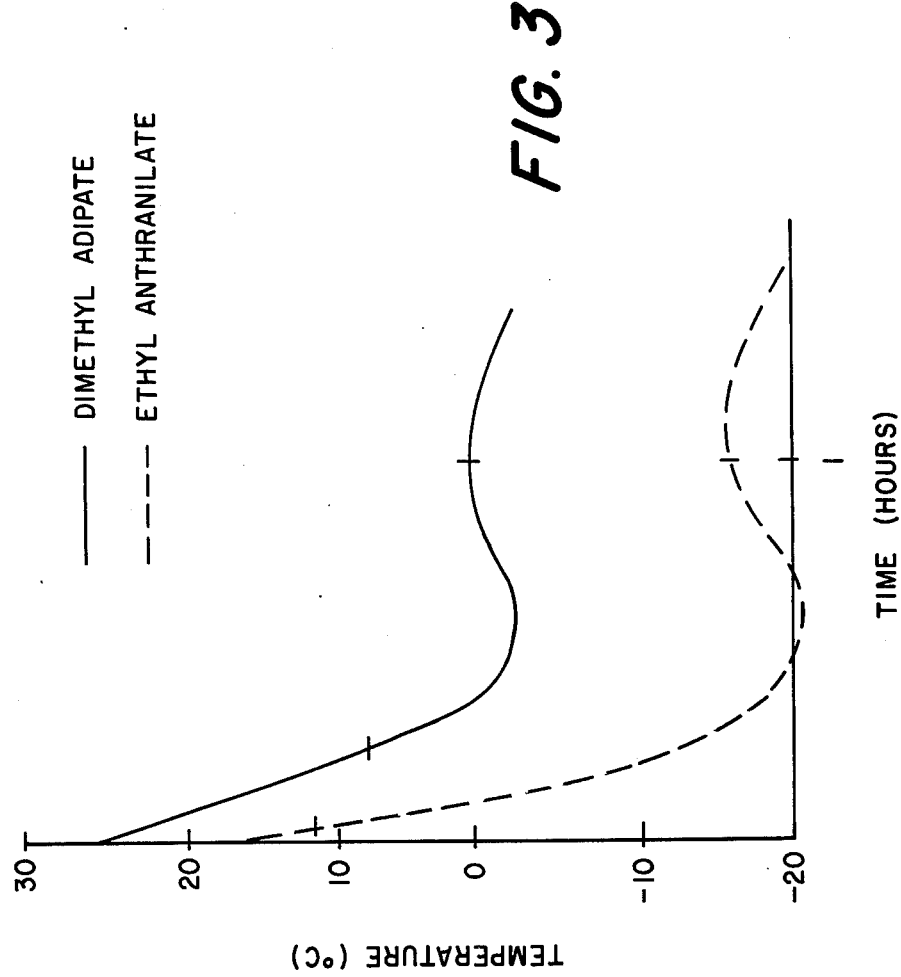

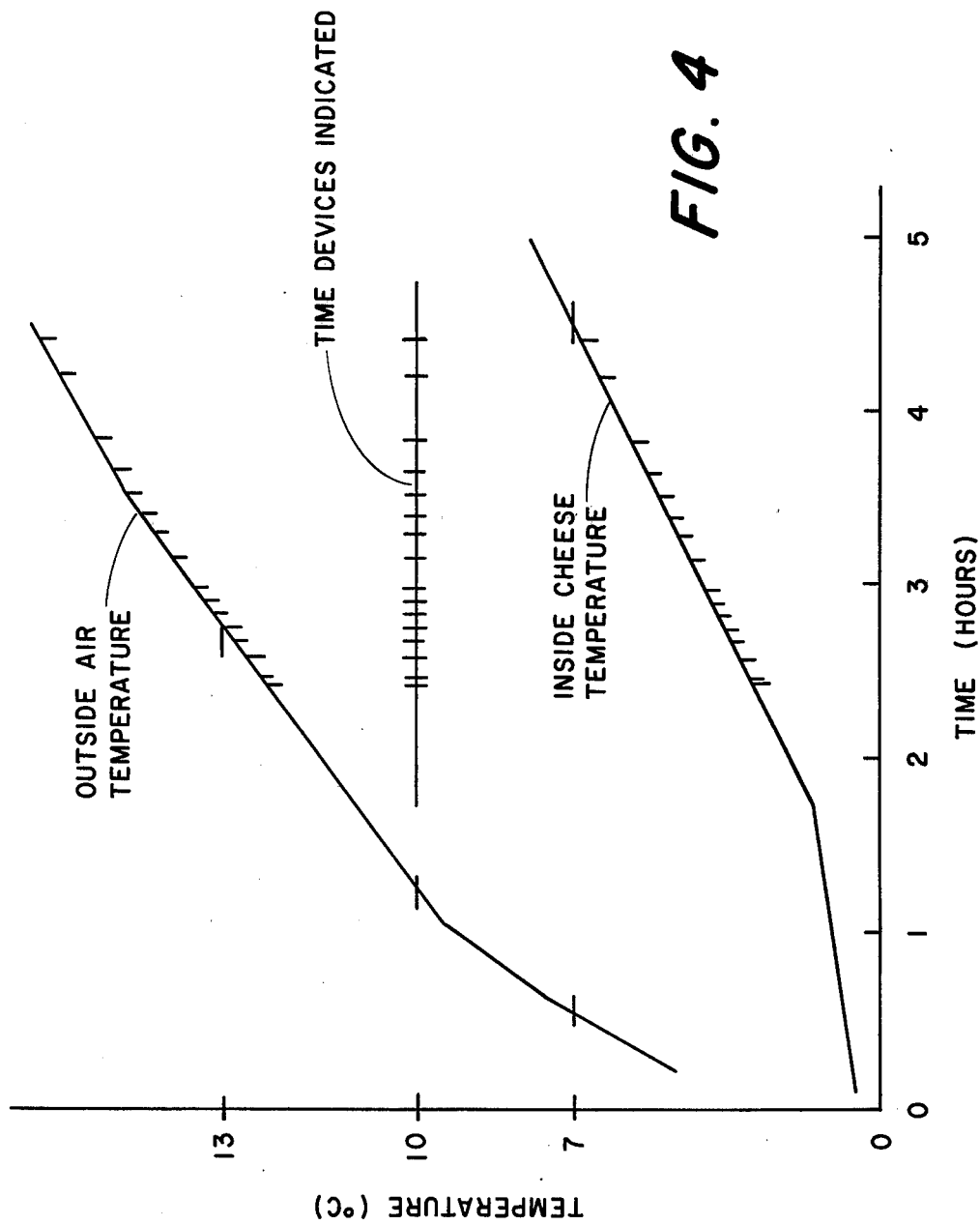

IRREVERSIBLE WARMUP INDICATOR

The invention described herein may be manufactured and used by or for the Government for Governmental purposes without the payment of royalties thereon.

BACKGROUND OF THE INVENTION

1. The Field of the Invention

The present invention generally relates to irreversible warmup indicators which, once warmed, indicate that a certain temperature has been exceeded even though the apparatus may later be recooled.

2. Description of the Prior Art

The prior art discloses many types of irreversible warmup indicators, but most are based on the fact that water expands as it is cooled from 4° C. to 0° C. When water is inclosed in a frangible container which is sealed, freezing of the water causes the container to break. Any increase in temperature causes the frozen water to thaw and indicate by wetting appropriately located filter paper. Such a device is exemplified by U.S. Pat. No. 3,786,777.

Similar devices make use of the fact that water flows at 0° C. or higher. For example, U.S. Pat. No. 2,560,537 discloses a strip of paper which is encased in a transparent tube with a crimp in its center. Water is placed in one section of the tube and the device is activated by freezing. Any thawing of the device causes the water to liquify and thereby flow by diffusion through the paper, producing an indication.

SUMMARY OF THE INVENTION

The invention comprises a gelatin capsule which is filled with an appropriately selected liquid which has a freezing point equal to the temperature to be monitored. The capsule is placed in proximity with an indicating paper. Dyestuff is dissolved in the liquid or is placed in powder form on the indicating paper. The apparatus is activated by freezing the liquid which is located in the capsule. Only those liquids which expand on thawing, contrary to water, are used in the apparatus. Therefore, after activation, thawing causes the liquid to expand and escape through the seam in the gelatin capsule, thereby causing the indicating paper to contact dissolved dye which irreversibly indicates that warming has occurred. The capsule and indicating paper are placed in a sealed glass tube which is enclosed in a plastic blister and cover. The plastic outer casing is then attached to or located in the environment which is to be monitored.

BRIEF DESCRIPTION OF THE DRAWINGS

It is the primary object of this invention to provide a reliable, inexpensive device which is able to indicate irreversibly that a certain temperature has been exceeded.

It is also the object of this invention to provide a device which is capable of selectively indicating that a plurality of different temperatures have been exceeded simply by altering the liquid indicator of the device.

It is a further object of the invention to provide an irreversible warmup indicator which can be stored for long periods of time without activation.

Figure 1:
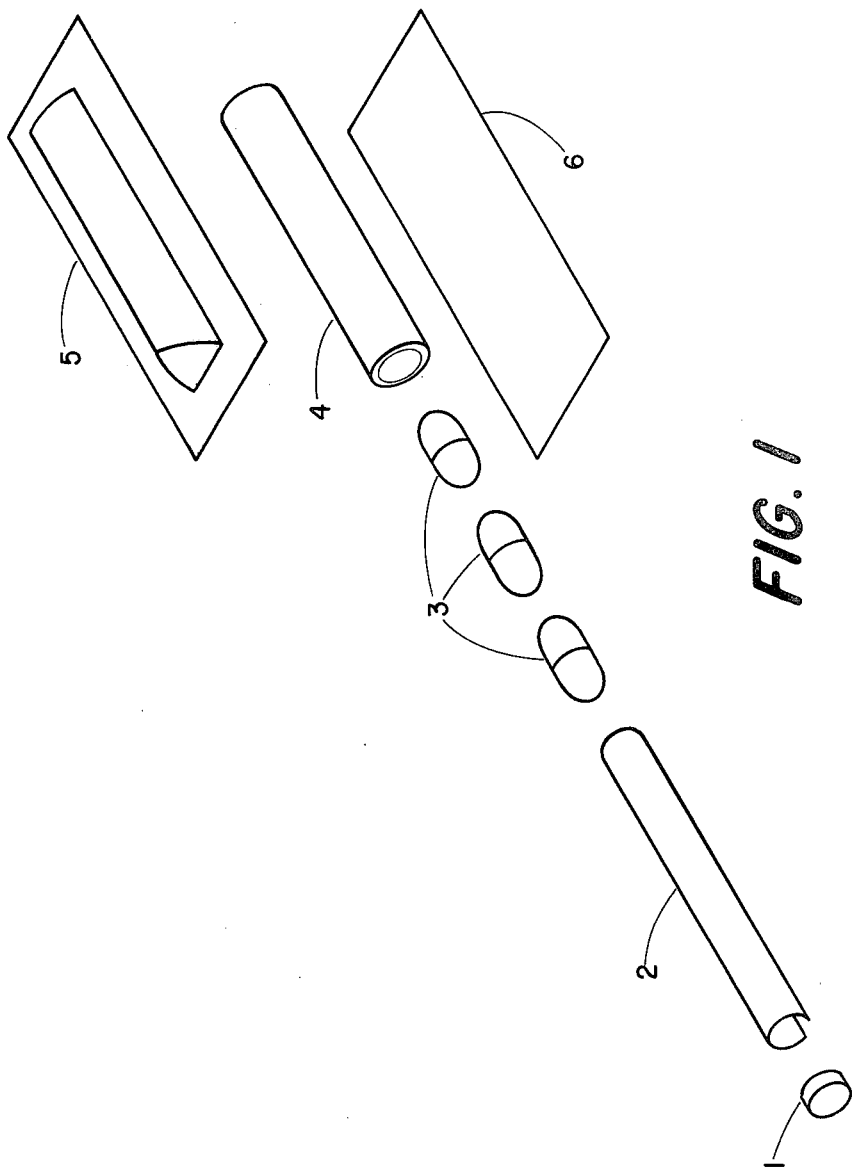
Figure 2:
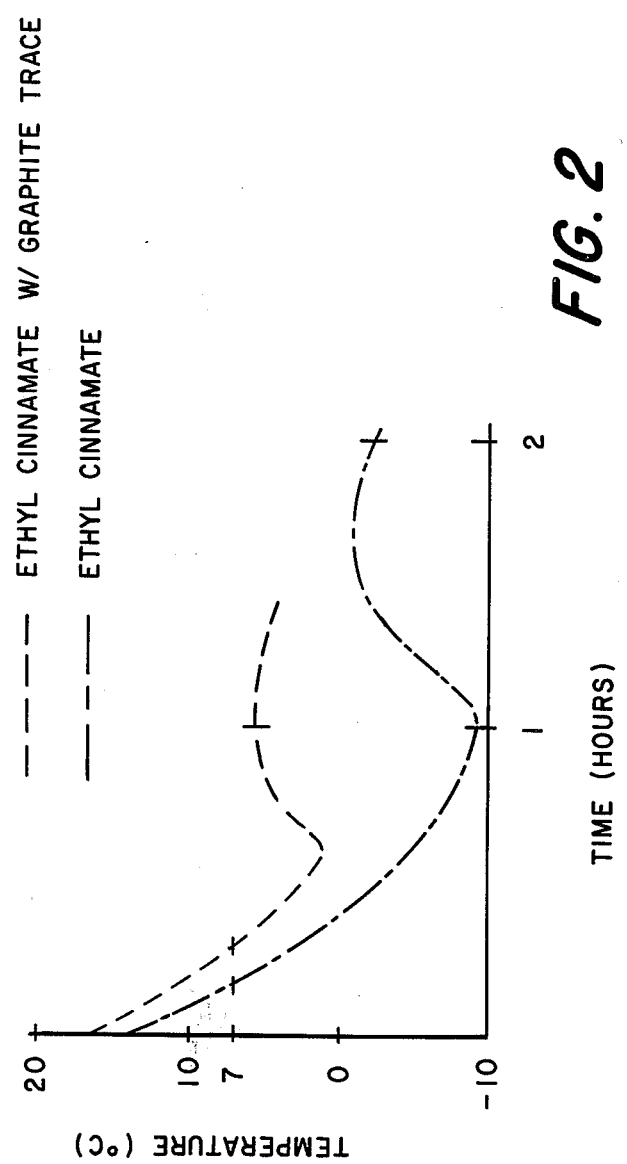

Other objects and features of this invention will become apparent to those skilled in the art by referring to the preferred embodiment described in the following specification and shown in the accompanying drawings in which:

FIG. 1 is a diagram of the apparatus immediately before assembly;

FIG. 2 is a graph of ethyl cinnamate as it is cooled in the pure state and in a state mixed with a trace of graphite;

FIG. 3 is a time graph of ethyl anthranilate and dimethyl adipate as they are frozen and thawed;

FIG. 4 is a graph showing the indication time of a plurality of 10° C. devices attached to the outside of a box containing cheese as compared to the inside and outside temperatures of a box as it is warmed.

DESCRIPTION OF THE PREFERRED EMBODIMENT

Referring to FIG. 1, gelatin capsules 3 are filled with the proper selected liquid having dye dissolved therein. When assembled, the capsules 3 are held inside glass tube 4, a strip of paper-aluminum foil laminate 2 covering one-half of the circumference of the capsules with the aluminum side of the laminate in contact with the capsules. The tube is closed by a Teflon plug 1. The plugged tube is located in a plastic blister 5 and covered with a plastic cover 6. The device is activated by freezing.

In this design the path between where the liquid is expelled from the capsule to the point of contact with the paper is considerably longer than with direct contact. When the liquid first leaves the capsule it tends to collect around the point of contact of the capsule joint and the glass tube. Traces of liquid remain there and at the interface with the aluminum foil and do not reach the paper. Larger amounts of liquid which are expelled when the device operates by melting of the liquid flow down the walls of the glass tube and are drawn into the paper by capillary action, producing the dye coloration on the paper. With this structure, loss of liquid, false indication (pre-spotting) by small amounts of liquid, and sudden volume changes of the encapsulated liquid are reduced.

The devices described herewith are based on an observation that liquids having a positive coefficient of expansion, when frozen in gelatin capsules and then melted, were partly expelled. One explanation for this action is that when the liquid freezes, with reduction in volume, air is drawn through the joint of the capsule. When melting occurs, the rapid increase in volume causes some of the melted liquid to flow out through the joint between the two parts of the capsule. This effect is exploited by incorporation of the dye in the liquid and surrounding the capsule with paper or other medium to which the dye is substantive. Alternatively, the paper can be impregnated with a dry dye soluble in the liquid and mixed with an inert white pigment such as titanium dioxide. Thus the temperature of indication is that at which the liquid melts and comes out of the capsule. It has been found, however, that other properties of the liquid must be considered in order to produce a stable, reliable indicator. The physical structure of the device is also of critical importance.

The following types of liquid properties are desirable:

(a) Melting Point. Melting must occur congruently at the temperature to be indicated.

(b) Tendency to Supercool. In order for a device to function, it must first be activated by freezing the liquid. Most organic liquids, in small closed volumes, must be subjected to a temperature below the melting point before freezing occurs. It is possible to control supercooling by addition of nucleating agents which initiate crystal growth.

(c) Volume Change When Frozen. A large contraction is desirable to draw air into the capsule when the liquid freezes. When melting occurs, the expansion of the liquid, as well as that of the air, expels some of the liquid through the cracks.

(d) Thermal Expansion of Liquid Phase. High thermal expansion of the liquid is undesirable, causing some liquid to be expelled as the ambient temperature fluctuates before activation. Unfortunately, most organic liquids have a relatively high thermal expansion of the order of 0.8 ml/liter/° C. This property has a significant effect on the shelflife. Preferred liquids have a large volume change on melting, but a nearly negligible thermal expansion of the liquid phase.

(e) Vapor Pressure. Liquids which have a significant vapor pressure at normal room temperature are lost from the device by evaporation during storage, thus reducing the shelflife.

(f) Viscosity. For best operation, the liquid viscosity is critical. If too low, the liquid may bleed through the joint over a period of time, leading to "pre-spotting" or spurious indication. If too viscous, it offers too much resistance to flowing through the joint and the device fails to indicate. In practice, the viscosity is adjusted by adding a small amount of an organic high polymer such as ethyl cellulose to the liquid. A viscosity of the order of 40 cps is used.

(g) Gelatin-Liquid Interphasial Tension. If the liquid wets the gelatin's surface too easily, it tends to bleed out through the cracks, resulting in pre-spotting and ultimately spurious indication as with low viscosity liquids. Liquid candidates were screened for this property by observing the spreading-contact angle-of a drop on the flat gelatin surface.

After dissolving the indicator dye and adjusting the viscosity, the liquid is transferred to the capsules by vacuum filling. The empty but closed capsules are submerged in the fill liquid and held below the surface by a wire grid. The vessel containing the fill liquid is then evacuated, which removes most of the air from the capsules. A slow release of the vacuum permits the liquid to flow into the capsules through the joints, nearly filling them. The filled capsules can then be washed with a suitable solvent such as methanol.

In order to prevent the liquid from being lost by evaporation and diffusion through a polyvinyl chloride blister, the capsules and indicator paper are enclosed in a sealed glass tube 4.

Table 1

| 7° C (45° F) DEVICE. Liquid Candidates for 7° Device | | | | |
|---|---|---|---|---|
| Liquid | MP° C Lit | MP° C Found | BP° C 760mm | Density g/ml (liq.) |
| O-Chlorobenzaldehyde | 12.1 | 8 | 212 | 1.248 |
| Citraconic Anhyclride | 7–8 | 7 | 213 | 1.247 |
| Decyl Alcohol | 5.5–6.5 | 5.5 | 229 | 0.8297 |
| Ethyl Anisate | 6.5–8.5 | 7–8 | 269 | 1.108 |
| Ethyl Cinnamate | 6.5–7.5 | 7.0 | 271 | 1.049 |
| Ethyl Myristate | 12.3 | 7.0 | 295 | 0.857 |
| 2-Hydroxy Acetophenone | 4.6 | 3.5 | 218 | 1.113 |
| Methyl Laurate | 3–5 | 2.7 | 262 | 0.8702 |
| Phenyl Cyclohexane | 7–8 | 5.5 | 235 | 0.9502 |

Table 1 shows the liquid candidates for use in this temperature range. Ethyl cinnamate was selected as the best overall liquid of the group based on the above discussed criteria. The full solution was modified by adding three percent of ethyl cellulose to increase the viscosity. FIG. 2 shows that by adding a trace of graphite as a nucleating agent, a reduction in the supercooling of ethyl cinnamate results. The liquid shows a 6.3 percent increase in volume on melting and has a thermal expansion coefficient of 0.818 ml/liter/° C.

For best results, the devices should be activated at 3° C. or below for a period of about 1 hour. The response of the device was found to be highly reliable. Eleven of a group of fourteen of the devices responded within the temperature range of 7° C. to 8.3° C.

Due to the thermal expansion and contraction of ethyl cinnamate during assembly and storage, it is preferred to store the unactivated devices with minimum exposure to temperature fluctuations. When stored under normal room conditions, 9 percent of a group of ninety-seven devices showed pre-spotting in eighteen days, and 16.5 percent showed a similar failure after 50 days.

Table 2

| 10° C (50° F) DEVICE. Liquid Candidates for 10° Device | | | | |
|---|---|---|---|---|
| Liquid | MP° C Lit | MP° C Found | BP° C 760mm | Density g/ml (liq.) |
| O-Chlorobenzaldehyde | 12.1 | 8 | 212 | 1.248 |
| Dimethyl Adipate | 10 | 10.3 | 113(13mm) | 1.060 |
| Ethyl Myristate | 12.3 | 7 | 295 | 0.857 |
| Nananoic Acid | 7–10 | 12.2 | 255 | 0.906 |
| Ethylene Dibromide | 9.85 | | 131.2 | 2.17 |
| 4-Methyl Quinoline | 9–10 | | 264 | 1.086 |

Liquid candidates for this temperature are shown in Table 2. Dimethyl adipate was chosen as the best all-around liquid. It was found that the pure liquid melts at 10.3° C., but some lots have been melting at points as low as 8° C. As illustrated in FIG. 3, the liquid has a minimum tendency to supercool, freezing at about 2° C. It shows less tendency to wet gelatin, which shows up as an improved shelf life. The liquid also shows that 2.7 percent increase in volume on melting and has a thermal expansion coefficient of 0.814 ml/liter/° C.

The reliability of the apparatus is almost 100 percent and activation occurs at 2° C., which can be obtained in a household refrigerator. Shelflife tests showed some failure during beginning periods due to pre-spotting. A group of 320 devices stored in a normal room with normal conditions showed a failure of 16 percent after 24 days and 32 percent after 56 days.

The best location to attach the irreversible warmup indicator on any shipping container must be determined by the specific environment to be monitored. For example, FIG. 4 shows tests which were done with sixteen 10° C. devices which were placed on the outside of a cheese container whose temperature was below 10° C. A thermocouple was placed in the center of the cheese carton to record its interior temperature. Another thermocouple was placed inside the test chamber maintained at 0° C. along with the cheese carton. The test chamber was allowed to warm up naturally to room temperature. It can be seen that, as expected, the indicators were monitoring the outside temperature of the box and not the surrounding air within the interior of the carton. The further into the carton the indicators are placed, the more they will monitor the contents of the box.

Table 3

| | 13° C (55° F) DEVICE. Liquid Candidates for 13° Device | | | |
|---|---|---|---|---|
| Liquid | MP° C Lit | MP° C Found | BP° C 760mm | Density g/ml (liq.) |
| Butyrophenone | 11.5–13 | 11.5 | 228 | 0.988 |
| Ethyl Anthranilate | 14.3 | 7.0 | 268 | 1.117 |
| Hexadecane | 17–18 | 17.2 | 287 | 0.773 |
| 2-Undecanone | 11–13 | 13 | 233 | 0.825 |
| P-Xylene | 13–26 | 13 | 138.35 | 0.854 |

The liquids tested for use in the 13° C. device are shown in Table 3. Ethyl anthranilate was selected as the best liquid in spite of its tendency to supercool, as shown in FIG. 3. The thermal expansion coefficient, 0.73 ml/liter/° C., is slightly less than the other liquids, but it has less tendency to wet the gelatin. Two percent of ethyl cellulose is added to increase the viscosity. The liquid shows a 2.8 percent increase on melting.

As a result of the supercooling of the devices, they must be activated in a deep freeze at −20° C. The devices were found highly reliable in their response. All of the group of twenty-one devices responded between 13° C. and 13.8° C. However, the shelflife is poor in the presence of temperature fluctuations in the storage area. It was found the devices stored after activation in a frozen state retained their activity without pre-spotting for at least 6 months. A group of 176 stored under fluctuating room conditions showed a failure of 40 percent after fourteen days and 54 percent after 48 days.

This device, due to the fact that it monitors temperature at and around 13° C., is especially useful for monitoring blood bags. Blood bags are normally shipped in insulated, ice-filled containers. Attaching a device to a wet, cool, flexible blood bag is possible with the use of adhesive tape. For most satisfactory results, a piece of double-sided adhesive tape is attached to the bag while empty and dry, and also a piece is attached to the indicator. Under these conditions, the tape will adhere to the bag permanently, and the piece of tape attached to the back of the indicator will easily adhere. After the bag is chilled and filled and the device is activated, the two pieces of tape stick together provided the chilled bag is wiped clear of water.

If more than one temperature is to be monitored, the device illustrated in FIG. 1 can be made with different liquids in each capsule, each liquid having a different dye color dissolved therein.

We claim:
1. An irreversible warmup indicator comprising:
 a. gelatin capsule having a seam therein;
 b. a strip of indicating paper-aluminum foil laminate covering one-half of the circumference of the capsule with the aluminum side of the laminate in contact with the capsule;
 c. a sealed glass tube containing said capsule and said laminate;
 d. a plastic outer casing containing said sealed glass tube;
 e. a liquid placed in said capsule with a melting point which is equal to the temperature to be monitored, said liquid having a positive thermal expansion coefficient in the temperature range immediately above its freezing point, whereby the apparatus is activated by freezing the liquid and a subsequent temperature rise causes thawing of the liquid, which expands and escapes through the seam in the capsule and contacts the indicating paper; and
 f. a dye, which is either dissolved in said liquid or is placed in powder form on said indicating paper.
2. The apparatus as described in claim 1 wherein said liquid is ethyl cinnamate.
3. The apparatus as described in claim 1 wherein said liquid is dimethyl adipate.
4. The apparatus as described in claim 1 wherein said liquid is ethyl anthranilate.
5. The apparatus as described in claim 1 wherein a dye is dissolved in said liquid.
6. The apparatus as described in claim 1 wherein said indicating paper is impregnated with a dry dye soluble in said liquid, said dry dye mixed with an inert white pigment.
7. The apparatus as described in claim 6 wherein said inert white pigment is titanium dioxide.
8. The apparatus as described in claim 2 wherein a dye is dissolved in the ethyl cinnamate.
9. The apparatus as described in claim 3 wherein a dye is dissolved in the dimethyl adipate.
10. The apparatus as described in claim 4 wherein a dye is dissolved in the ethyl anthranilate.

* * * * *